United States Patent
Tzean et al.

(10) Patent No.: US 6,168,947 B1
(45) Date of Patent: Jan. 2, 2001

(54) NEMATOPHAGOUS FUNGUS *ESTEYA VERMICOLA*

(75) Inventors: Shean Shong Tzean, Taipei; Jun-Yang Liou, Keelung; Ju-Ying Shih, Kaohsiung, all of (TW)

(73) Assignee: Food Industry Research and Development Institute (TW)

( * ) Notice: Under 35 U.S.C. 154(b), the term of this patent shall be extended for 0 days.

(21) Appl. No.: 09/248,575

(22) Filed: Feb. 11, 1999

(51) Int. Cl.$^7$ .................................................. C12N 1/14
(52) U.S. Cl. ........................................................ 435/254.1
(58) Field of Search .......................................... 435/254.1

(56) References Cited

U.S. PATENT DOCUMENTS 5,360,607   11/1994   Eyal et al. ........................ 424/93.5

FOREIGN PATENT DOCUMENTS 0 494 592 A1   7/1992   (EP) ............................. A01N/63/04
WO 94/28725   12/1994   (WO) ............................ A01N/63/04

OTHER PUBLICATIONS

Schol–Schwarz M.B. Personia. 1970. vol. 6, Part 1, pp. 59–94.*
Wingfield M.J. Mycologia. 1987. vol. 79, No. 2, pp. 325–328.*
Cole et al., "Taxonomic Studies of Phialophora", Mycologia, 1973, 65:661–688.
Crous et al., "Phaeoacremonium gen. nov. associated with wilt and decline disease of woody hosts and human and human infections", Mycologia, 88(5):786–796 (1996).
Gams et al., "Phialemonium, A New Anamorph Genus Intermediate Between Phialophora and Acremonium", Mycologia, 75(6):977–987, 1983.
Jaffee et al., "Parasitism of the Nematode *Criconemella xenoplax* by the Fungus *Hirsutella rhossilinesis*", Phytopathology, 72(10):1378–1381, 1982.
Mamiya, "Pathology of the Pine Wilt Diseas Caused by *Bursaphelenchus xylophilus*", Ann. Rev. Phytopathol., 21:201–220, 1983.
Dorenbosch, "Key to Nine Ubiquitous Soil–Borne Phoma–Like Fungi", Persoonia, vol. 6, part 1, p. 1 1970.
Yan et al., "Assessment of Philophora species based on ribosomal DNA internal transcribed spacers and morphology", Mycologia 87(1):72–83, 1995.
Patent Abstracts of Japan vol. 007, No. 95 (C–163), Aug. 23, 1983, JP 58 023611 A (Tomoe Kagaku Kogyo KK), Feb. 12, 1983, abstract.

* cited by examiner

*Primary Examiner*—Irene Marx
*Assistant Examiner*—Vera Afremova
(74) *Attorney, Agent, or Firm*—Fish & Richardson P.C.

(57) ABSTRACT

A fungus which has high infectivity toward a stem, leaf, bud, or flower nematode and is characterized by the production of a first type of conidiophores, conidiogenous cells, and conidia and a second type of conidiophores, conidiogenous cells, and conidia when grown in vivo or on a solid medium. The first type of conidiophores is macronematous, mononematous, simple, erect, and broadly ampulliform; the first type of conidiogenous cells is integrated, phialidic, and rarely percurrent; and the first type of the conidia is solitary, one-celled, asymmetrically ellipsoidal, lunate, and concave. The second type of conidiophore is macronematous, mononematous, simple or branched, cylindrical, subulate, and elongate; the second type of conidiogenous cells is integrated, phialidic, enteroblastic, terminal or intercalary, laterally proliferic, and indeterminate; and the second type of conidia is solitary, one-celled, bacilloid, and cylindrical. In particular, a fungal culture *Esteya vermicola* ATCC74485.

16 Claims, 5 Drawing Sheets

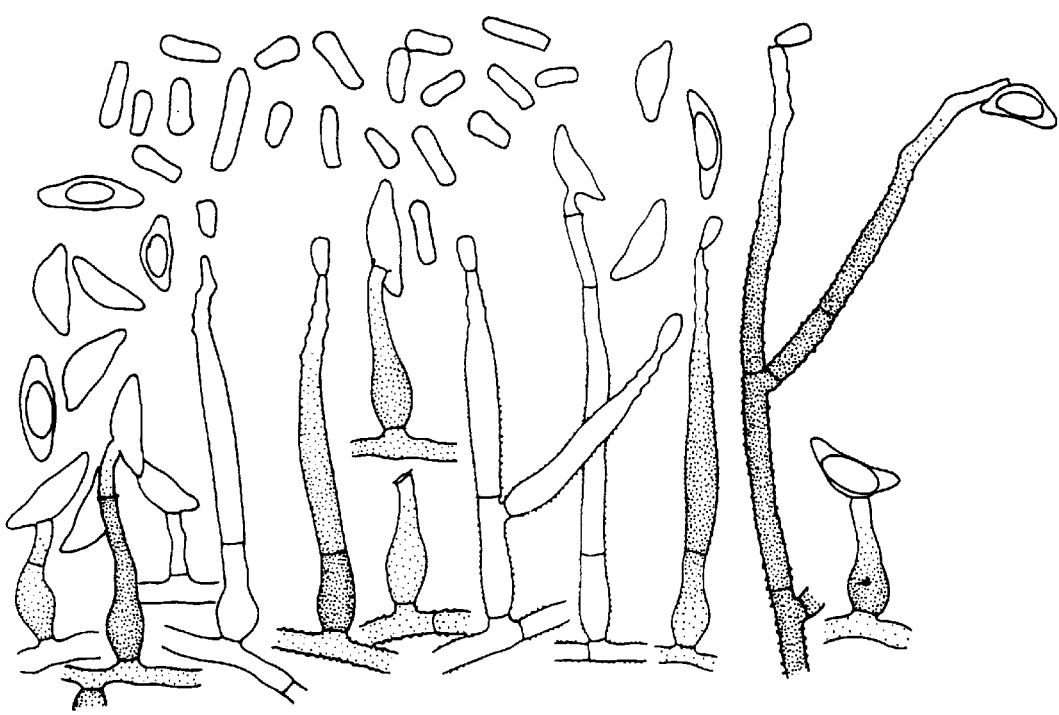
FIG. 1  20μm
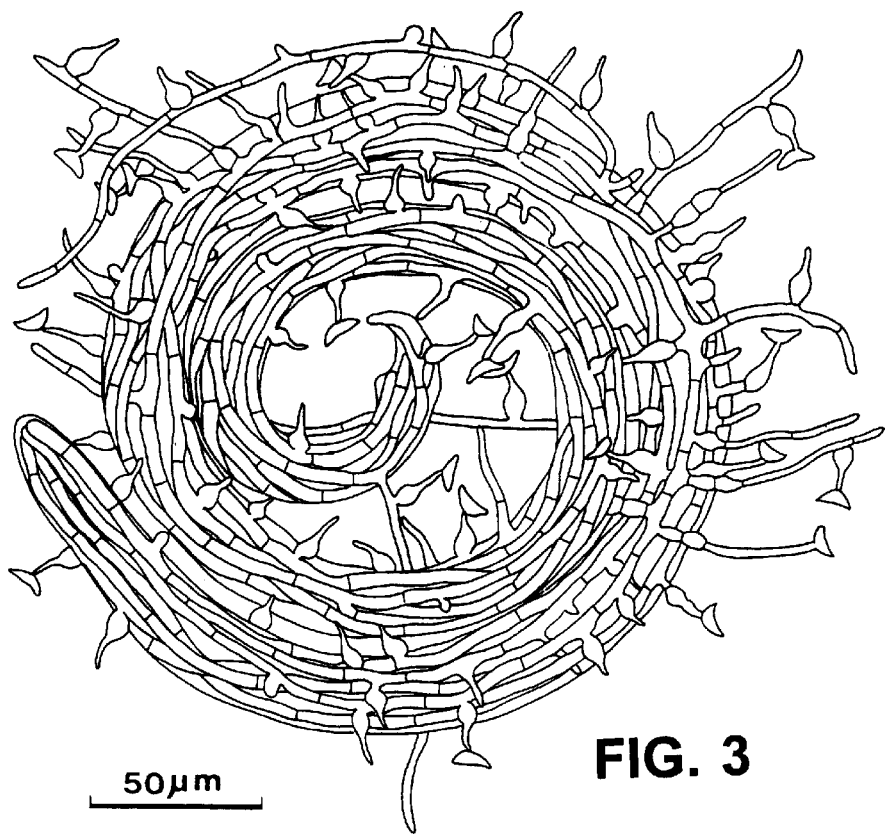
50μm  FIG. 3

NEMATOPHAGOUS FUNGUS *ESTEYA VERMICOLA*

BACKGROUND OF THE INVENTION

The wilting disease of pine trees caused by the pinewood nematode, *Bursaphelenchus xylophilus* is widespread in eastern Asia. According to an estimation made in Japan in 1981, the annual loss of native pine stands, e.g., Japanese red pine, *Pinus densiflora* Sleb. & Zucc., Japanese black pine, *P. thunbergii* Parl. and Luchu pine, *P. luchuensis* Mayr., was approximately 2 million m$^3$, with the death of nearly 10 million trees. In Japan, the first occurrence of pine wilt disease was documented in 1905 in Nagasaki, Kyushu. At that time, the cause of this devastating disease of pine trees was not understood. Inoculation experiments demonstrated that the pinewood nematode *B. xylophilus* was the causal agent responsible for the epidemics of pine tree wilt. Further studies have determined the disease cycle of the pine tree wilt.

SUMMARY OF THE INVENTION

This invention features a new fungus which has high infectivity toward a stem, leaf, bud, or flower nematode and is characterized by the production of a first type of conidiophores, conidiogenous cells, and conidia and a second type of conidiophores, conidiogenous cells, and conidia when grown in vivo or on a solid medium.

More specifically, the first type of conidiophores is macronematous, mononematous, simple, erect, and broadly ampulliform; the first type of conidiogenous cells is integrated, phialidic, and rarely percurrent; and the first type of the conidia is solitary, one-celled, asymmetrically ellipsoidal, lunate, and concave; and the second type of conidiophore is macronematous, mononematous, simple or branched, cylindrical, subulate, and elongate; the second type of conidiogenous cells is integrated, phialidic, enteroblastic, terminal or intercalary, laterally proliferic, and indeterminate; and the second type of conidia is solitary, one-celled, bacilloid, and cylindrical. A fungus of this invention can be further characterized by the production of blastospores when grown in liquid broth.

More detailed features of the two types of cells include: The first type of conidiophores is macronematous, mononematous, simple, erect, broadly ampulliform, tapering upward into a thin neck, subhyaline to greyish green, and smooth, roughened to very roughened; the first type of conidiogenous cells is integrated, phialidic, and rarely percurrent; the first type of conidia is solitary, one-celled, asymmetrically ellipsoidal, lunate, concave, hyaline, smooth-walled, and adhesive, and ends moderately apiculate and contains an endospore-like structure; the second type of conidiophores is macronematous, mononematous, simple or branched, erect, cylindrical, subulate, septate, hyaline, subhyaline to greyish green, smooth, roughened to very roughened, and is somewhat swollen at the base; the second type of conidiogenous cells is integrated, phialidic, enteroblastic, terminal or intercalary, laterally proliferic, and indeterminate; and the second type of conidia is solitary, slimy, one-celled, bacilloid, cylindrical, hyaline, smooth, and non-adhesive, and often aggregates at the apex forming false head.

The fungus of this invention can infect nematodes such as pinewood nematode *B. xylophilus*; rice white tip nematode *Aphelenchoides besseyi*; pseudopinewood nematode *Bursaphelenchus mucronatus*; rice stem nematode *Ditylenchus angustus*; strawberry, wheat, corn, tobacco, tomato, and sugarbeet stem nematode *Ditylenchus dipsacis*; red ring nematode of coconut palms *Phadinaphelenchus cocophilus*; strawberry nematode *Aphelenchoides fragariae* or *Aphelenchoides ritzemabos*; and other morphologically or habitually closely related stem, leaf, bud and flower nematodes.

A fungus of this invention, a strain of *Esteya vermicola*, was deposited with the American Type Culture Collection 10801 University Boulevard, Manassas Va. 20110-2209, U.S.A., on Jan. 29, 1999 and assigned accession number 74485. It was also deposited with the Culture Collection and Research Center, Taiwan, on Feb. 4, 1999 (accession number CCRC 930028). Contemplated within the scope of this invention are mutants derived from the deposited strain (obtained by conventional or recombinant methods), as well as any fungi which have identifying characteristics of the deposited strain.

All fungi of this invention, including the deposited strain and its mutants, are nematophagous and can be used as biocontrol agents against nematodes. Other features of the present invention will be apparent from the following drawings, detailed description, and the appending claims.

BRIEF DESCRIPTION OF THE DRAWING

FIG. 1 shows two types of conidiophores and conidia of *Esteya vermicola*.

FIG. 3 shows conidiophores, conidiogenous cells, and conidia of *Esteya vermicola* arising from an infected nematode.

DETAILED DESCRIPTION OF THE INVENTION

Figure 2:
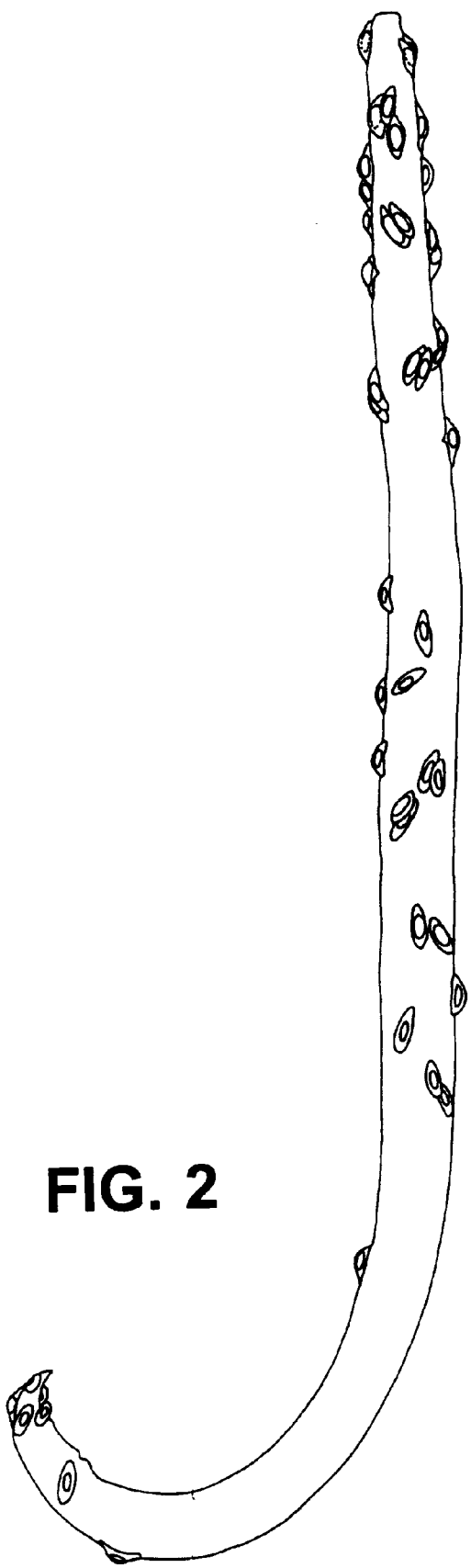
FIG. 2 shows conidia of *Esteya vermicola* attached to a nematode cuticle.

The first occurrence of this disease was found in Taiwan in 1985 in northern areas. Now the disease is widespread and claims a 50–60% or even higher mortality in this Country. To prove the pathogenicity using Koch's postulates, retrieval of the pinewood nematodes from wilting pine trees was a first step and a regular practice in our laboratory. On one occasion, a population of the pinewood nematode, *B. xylophilus*, recovered from a wilting black pine tree, was established on a mycelia sterile fungal culture on potato dextrose agar (PDA) (Difco) slants. Unaccountably, the population was found completely diminished after incubation at room temperature for 2–4 weeks. Examination of the pinewood nematodes cadavers in this population revealed the infestation of an endoparasitic hyphomycete. Axenic culture of the endoparasite was obtained by a single or mass spores isolation technique. The pigmented endoparasite in vivo and in vitro produced two types of conidiophores, conidiogenous cells, and conidia, but varied in their proportion. The first type of conidiogenous cells consisted of an inflated, subglobose to globose base and abruptly attenuated thin neck, the neck incollarate. The conidia were lunate, concave, containing a distinct endospore-like apparatus. The second type of conidiophores were mononematous, simple or branched. Conidiogenous cells were discrete or integrate, elongate, subulate, 3–7 septate, the base with or without inflation, the apex smooth or warted. The conidia were cylindrical to bacilloid. Superficially, the endoparasite bears some resemblance to Phialophora Medlar, but can be distinguished readily by the morphological characters in the sporulating structures, conidia, and in its biology and habitats. Since the endoparasite can not be accommodated to any described parasites of microscopic animals, a new genus is erected to accommodate this organism.

Without further elaboration, it is believed that the above description has adequately enabled the present invention. The following specific example is, therefore, to be construed as merely illustrative, and not limitative of the remainder of the disclosure in any way whatsoever. All of the publications cited herein are hereby incorporated by reference in their entirety.

Monoxenic Culture of the Pinewood Nematode, *B. xylophilus*

Pieces of wood cores, about 5–8 cm in length, 0.3 mm in diameter, were retrieved from pinewood nematode-infected and wilted Japanese black pine trees with an increment borer in Yangmingshan, Taipei, Taiwan, on September 1995. The pieces of wood cores were cut into small segments, ca. 0.5–1 cm in length, and were dipped into tap water in petri dishes. The dishes were incubated at room temperature (ca. 24–27° C.) for 24 hrs. An abundance of pinewood nematodes released from the wood tissues into the tap water were picked up with a very fine spirally etched metal needle, and transferred to 1% sodium hypochlorite for surface deinfestation for 2–3 min, and rinsed with sterile distilled water three times, each time ca. 5 min. The presumably axenic pinewood nematodes were finally transferred to mycelia sterile fungal culture on PDA slants, and incubated at 25° C. without illumination to establish the population. The established nematode populations were subcultured at the intervals of every 3–4 weeks, and maintained for inoculation experiments.

Isolation, Culturing, Diagnosis and Illustration of the Hyphomycete Endoparasite The pinewood nematode cadavers infested with the fungal endoparasite were spread onto a 2% water agar plate. The attached conidia were isolated singly or in mass under a stereomicroscope, and transferred to PDA slants. The pure fungal cultures were incubated at 25° C. for 2–3 weeks, and their morphological characteristics were diagnosed and illustrated under a compound light microscope (Olympus BH-2) with the aid of an drawing tube (Olympus), at the magnification of 400× or 1000×. The sporulating structures and conidia of the endoparasite produced from the inoculated and infected pinewood nematodes were also diagnosed and illustrated by the method mentioned above. The color nomenclature corresponds to that of Kornerup, A. & Wanscher, J. H. (1978). *Methuen Handbook of Colour*. Eyre Methuen Ltd: London, U.K.

Parasitism of *B. xylophilus* by the New Fungal Endoparasite

The fungal endoparasite was maintained on PDA slants either at 4° C. or room temperature. For the test of infectivity, the endoparasite was first subcultured to one tenth strength corn meal agar (CMA) (Difco) plates or slants at 25° C. for ca. 2–3 weeks. A pieces of agar disc bearing proliferic mycelia was excised and inoculated onto the center of a 2% water agar plate. The plate after incubation at 25° C. about 7–10 days, the colony produced an adequate amount of lunate, adhesive conidia, and was infested with 250–300 pinewood nematodes in 10 $\mu$l suspension. The inoculated plates were examined at intervals of 2, 4, 6, 8, 16, 24 hrs, and 2, 4, 7 days under a light microscope. The infection rate was recorded. The nematodes infected by the endoparasite at different developing stages were picked up and mounted in water, and were examined by light microscopy and photography for the mode of parasitism. To examine the parasite or host-parasite interactions by scanning electron microscope (SEM), a previously described method was used. Tzean, S. S. & Estey, R. H. (1978). *Schizophyllum commune* Fr. as a destructive mycoparasite. *Canadian Journal of Microbiology* 24, 780–784.

Taxonomy

Esteya (genus circumscription)

Deuteromycotina, Hyphomycetes, with ascomyceteous affiliation, conidiophores, conidiogenous cells, and conidia of two types. First type conidiophores macronematous, mononematous, simple, erect, broadly ampulliform; conidiogenous cells integrated, phialidic, rarely percurrent; conidia solitary, one-celled, asymmetrically ellipsoidal, lunate, concave. Conidiophores of the second type macronematous, mononematous, simple or branched, cylindrical, subulate, elongate; conidiogenous cells integrated, phialidic; enteroblastic; terminal or intercalary, laterally proliferic, indeterminate; conidia solitary, one-celled, bacilloid, cylindrical.

*Esteya vermicola* (species circumscription) Colonies on potato dextrose agar (PDA) growing moderately, after 7 days at 25° C., 3.5–4.5 mm in diameter, grey, greyish green to dark green (27F6-7; 27EF1-3); reverse grey to dark green (28F4-5; 30F1-4). Hyphae branched, septate, hyaline, subhyaline to greyish green, smooth, roughened to very roughened, 2–4 $\mu$m wide. Conidiophores, conidiogenous cells, and conidia of two types. First type conidiophores macronematous, mononematous, simple, erect, broadly ampulliform, (10–)16–29(–62)×(1.5–)3–4.4 $\mu$m, tapering upward into a thin neck, 1.5–1.9 $\mu$m wide, subhyaline to greyish green, smooth, roughened to very roughened; conidiogenous cells integrated, phialidic, rarely percurrent; conidia solitary, one-celled, asymmetrically ellipsoidal, lunate, concave, ends moderately apiculate, hyaline, smooth-walled, 8.2–11.1×3.5–3.7 $\mu$m, containing an endospore-like structure, adhesive. Conidiophores of the second type macronematous, mononematous, simple or branched, erect, cylindrical, subulate, septate, hyaline, subhyaline to greyish green, smooth, roughened to very roughened, (22.2–)34.1–43 $\mu$m long, 3–4.4 $\mu$m wide at base, 1.48 $\mu$m wide at tip; conidiogenous cells integrated, phialidic, enteroblastic, terminal or intercalary, laterally proliferic, indeterminate; conidia solitary, slimy, one-celled, bacilloid, cylindrical, hyaline, smooth, (3–)4.4–7.4×1.5–1.9 $\mu$m, non-adhesive, often aggregate at the apex forming false head. In liquid broth, except the lunate and rod-shaped conidia, the cells are capable of producing blastospores in tremendous numbers. The blastospore, when subcultured onto solid medium with poor nutrients, germinates and generates lunate adhesive conidia. Nematodes parasitized by adhesive, lunate conidia. In vivo in infected nematode host, the first type conidiophores, conidiogenous cells, and conidia predominate; the morphological characteristics are comparable to those produced on the cultural medium.

Habitat: Parasitic on pinewood nematodes.

Etymology: The genus is named in honor of Professor emeritus R. H. Estey, Macdonald College, McGill University, Canada, in recognition of his contribution to the study of nematophagous fungi and nematology; the species is named in reference to the capability of the fungus to parasitize nematodes.

Specimen examined: From infected pinewood nematodes, *B. xylophilus*, extracted from a wilted Japanese black pine tree, *Pinus thunbergii*, in Yanmingshan, Taipei City, Sep. 10, 1995; holotype PPH30 (dried culture) and extype (living culture) were deposited in the Department of Plant Pathology and Entomology, National Taiwan University, Taipei, Taiwan, and the Culture Collection and Research Center, Taiwan (accession number CCRC 930028).

Parasitism

Figure 4:
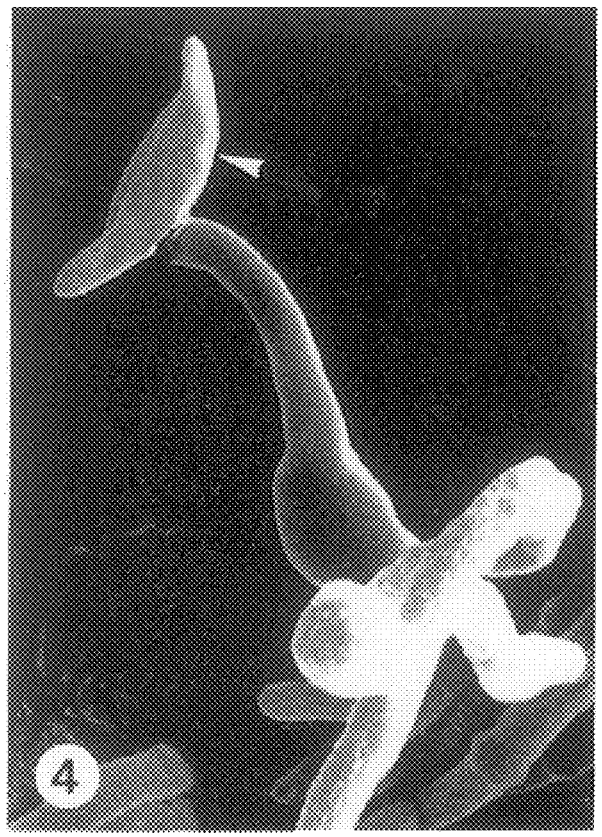
FIG. 4 shows an asymmetrically ellipsoidal, apiculate conidium of *Esteya vermicola*, produced on the tip of flask-shaped phialidic conidiogenous cell (arrow head); bar=5 µm.
Figure 5:
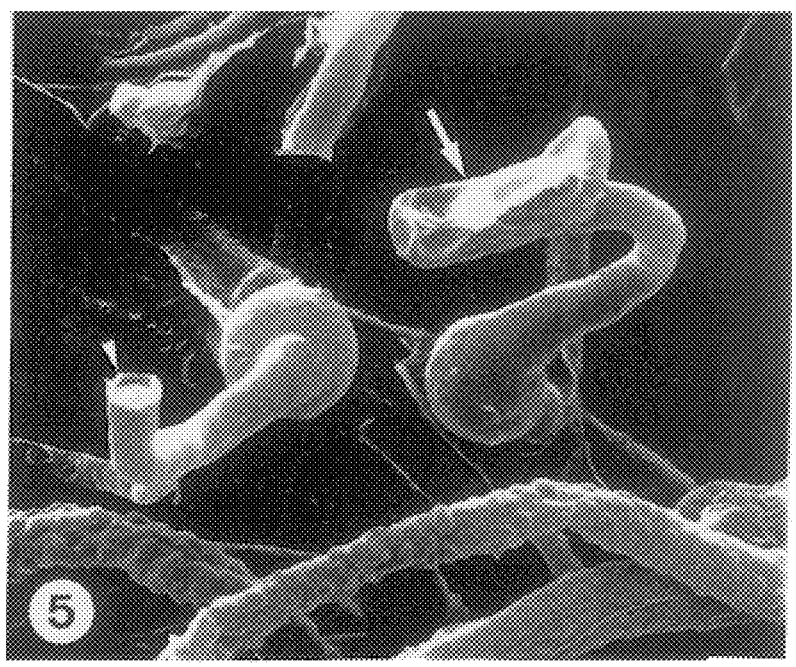
FIG. 5 shows the second type of flask-shaped, phialidic, conidiophores of *Esteya vermicola* with a distinct opening of the conidiogenous cell (arrow head), and an attached asymmetrically ellipsoidal conidium (arrow); bar=5 µm.
Figure 6:
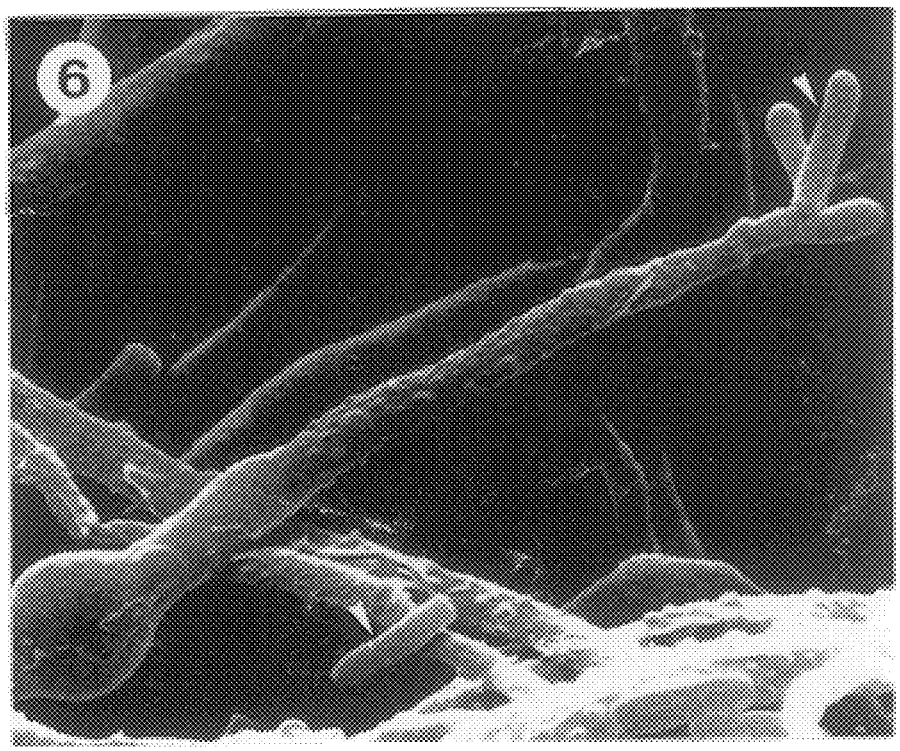
FIG. 6 shows first type of conidiophores of *Esteya vermicola* with rod-shaped conidia (arrow heads); bar=5 µm.
Figure 7:
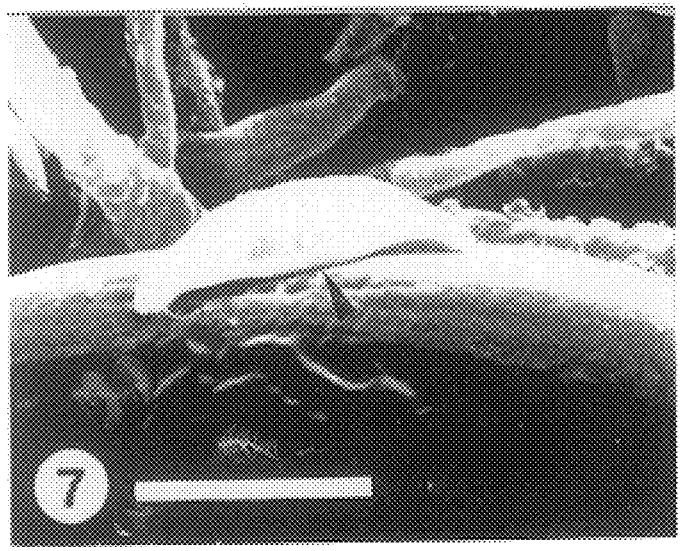
FIG. 7 shows a conidium of *Esteya vermicola* attached to the cuticle of a nematode (arrow head); bar=5 µm.
Figure 8:
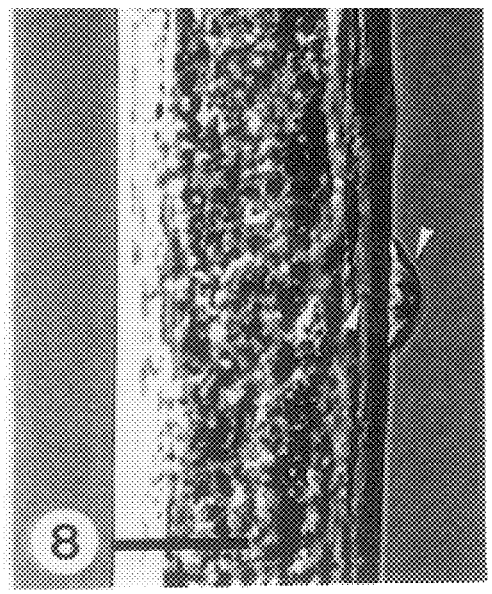
FIG. 8 shows infection peg initiated from a conidium of *Esteya vermicola* penetrating the cuticle and muscle layer of a nematode (arrow heads); bar=10 µm.
Figure 9:
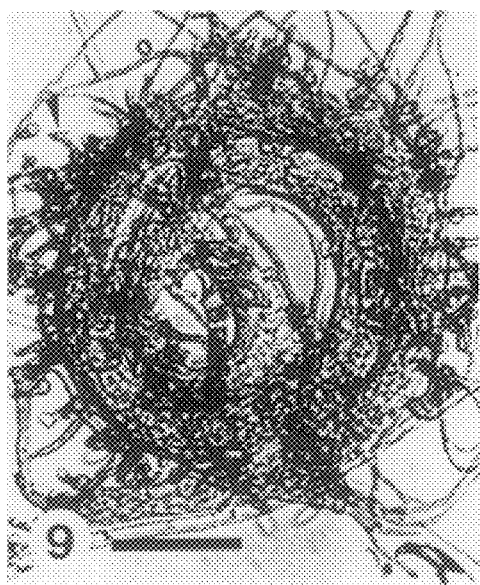
FIG. 9 and FIG. 10 show conidiophores and conidia (arrow heads) of *Esteya vermicola* arising from an infected nematode; bar=50 and 20 µm, respectively.
Figure 10:
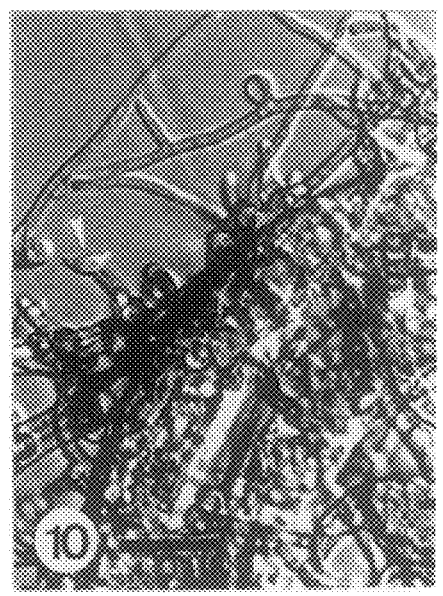

*Esteya vermicola* produced colonies with sparse mycelium, and predominately discrete, flask-shaped conidiogenous cells and lunate, concave adhesive conidia in nutrient-poor water agar plates (FIGS. 1, 4, and 5). In such plates, numerous lunate conidia readily adhered to the pinewood nematodes by adhesive mucilage on the concave side when the nematodes migrated and touched the conidiogenous cells and conidia. Ninty percent of the infested nematodes were found attached and infected by the adhesive conidia within 24 hrs (FIG. 2). Attachment of the conidia to the nematodes host was random over the length of body, although the head and tail regions appeared to be the preferred sites (FIG. 2). After attachment for 18–24 hrs, the conidia germinated and penetrated the nematode cuticle by a fine infection peg, and produced a subcutaneous infection bulb, from which two or three trophic hyphae initiated (FIGS. 7 and 8). The nematode was killed after the infection hyphae ramified extensively and destroyed the organs and tissues. Usually within 8–10 days after infestation (FIGS. 3, 9, and 10), almost 100% of the nematode population was wiped out. Upon emergence from the killed nematode, the hyphae produced almost exclusively the discrete, flask-shaped conidiogenous cells and lunate, adhesive conidia (FIGS. 3 and 10). In the nutrient rich culture medium, *E. vermicola* mainly produced the elongate, subulate, multi-septate conidiogenous cells and the cylindrical to bacilloid, non-adhesive conidia (FIGS. 1 and 6). None of the infested nematodes were found invaded by this type of conidia.

Superficially, *E. vermicola* in having an olivaceous green to black colony and pigmented flask-shaped to cylindrical, subulate conidiogenous cells resembles some *Phialophora* species. Schol-Schwarz, M. B. (1970). *Persoonia* 6, 59–94; G. T. & Kendrick, B. (1973). *Mycologia* 65, 661–688; Iwatsu, T., Udagawa, S. I. & Toyazaki, N. (1988). *Mycotaxon* 32, 439–445; Millar, K. R. (1990). *Mycologia* 85, 647–650. However, in Phialophora, the conidiogenous cells constricted at the neck and opened with a distinct cup- or beaker-shaped collarate is in distinct contrast to those of Esteya. One of the *Phialophora* species which most resembles *E. vermicola* was *P. bubakii* (Laxa) Schol-Schwarz. Schol-Schwarz, M. B. (1970). It produces two types of conidiogenous cells and several types of conidia. The primary phialides are flask-shaped, smooth or warted, producing cylindrical to allantoid conidia. The secondary phialides are cylindrical, tapering, ending in a sharp point with an indistinct collarette with age, and produced ovoid to spherical conidia. *P. bubakii* is also characterized by moniliform hyphae, synnematous conidiophores and microsclerotia. Despite similarities, apparently *E. vermicola* can be distinguished from *P. bubakii* by the microscopic features in the sporulating apparatus and conidia as well. Occasionally, the phialides in some species of *Phialophora* were proliferic and percurrent, and conidia were dimorphic or variable in shape and size according to age, culture medium or culture conditions [Schol-Schwarz (1970); Cole & Kendrick (1973)]. The same events also occurred in *E. vermicola*, thus calling the attention to the precaution and standardization necessary for verification of the identification. Most *Phialophora* species were saprobic, and have been isolated from air, water, soil and stored pine timber or the wood of Betula, Pinus, Picea, Abies, Populas, Fagus, etc., but some were human pathogens. Schol-Schwarz (1970); Cole & Kendrick (1973). Two endoparasitic *Phialophora* species, *P. endoparasitica* Barron & Szijarto and *P. tribrachispora* Barron & Szijarto, have been described from bdelloid rotifers, both characterized by bottle-shaped phialides opened with prominent membranous collaratte, and appendaged conidia, Barron, G. L. & Szijarto, E. (1982). *Canadian Journal of Botany* 60, 1212–1215; Barron, G. L. & Szijarto, E. (1984). *Mycologia* 76, 1107–1100. More recently these two species have been transferred to a new genus Haptospora Barron, typified by *H. appendiculata* Barron, which is also a rotifer endoparasite, Barron, G. L. (1991). *Canadian Journal of Botany* 69, 503–506. Biologically and ecologically, these species are more closely related to *E. vermicola*. The phylogenetic relationships among them merit further investigation using rDNA molecular techniques. Yan, Z. H., Rogers, S. 0. & Wang, C. J. K. (1995). *Mycologia* 87, 72–83.

The morphological characters of *E. vermicola* are also somewhat similar to Phaeoacremonium W. Gams, Crous et M. J. Wingf., and Phialemonium W. Gams & McGinnis, two genera intermediate between Phialophora and Acremonium Link: Fr., which possess pigmented conidiogenous cells and inconspicuous collarettes. These genera were saprobic or pathogenic, causing human infection, or attacking woody plants resulting in stunting or dieback. Biologically, they appeared not related to any nematode endoparasitic fungi. Crous, P. W., Gams, W., Wingfield, M. J. & Wyk, P. S. van. (1996). *Mycologia* 88, 786–796; Gams, W. & McGinnis, M. R. (1983). *Mycologia* 75, 977–987.

The genus Hirsutella was mostly entomopathogenic [Minter, D. W. & Brady, B. L. (1980). *Transactions of the British Mycological Society* 74, 271–282; Evans, H. C. & Samson, R. A. (1986). *Canadian Journal of Botany* 64, 2098–2103] except *Hirsutella rhossiliensis* Minter & Brady has been reported capable of parasitizing the ring nematode *Criconemella xenoplax* (Roski) Luc & Rasiisan, and the cyst nematode, *Heterodea schachtii* Schmidt. Jaffee, B. A. & Zehr, E. I. (1982). *Phytopathology* 72, 1378–1381; Jaffee, B. A. & Zehr, E. I. (1985). *Journal of Namatodology* 17, 341–345; Jaffee, B. A. & Muldoon, A. E. (1989). *Journal of Nematology* 21, 505–510). Hirsutella can be mononematous or synnematous, mono- or polyphialidic. Minter & Brady (1980). The conidiogenous cells of *H. rhossiliensis* are sessile, arising more or less perpendicularly singly from the vegetative hyphae, which are hyaline, smooth, or slightly verrucose towards the long, thin apex, the base swollen. The conidia are unicellular, hyaline, ellipsoid, often in the shape of an orange segment, borne on the neck singly or in a group, enveloped in a pigmented mucous sheath. Minter & Brady (1980). These characters are reminiscent of the flask-shaped conidiogenous cells and lunate adhesive conidia of *E. vermicola*. However, the lunate conidia lack the coating of a mucous sheath, and the adhesive mucilage is only presented on the concave side. The localization of an adhesive at specific site also has been reported in the nematode-endoparasite Drechmeria coniospora (Drech.) W. Gams & Jansson, which used an adhesive knob at the distal end of the conidia to adhere to the nematode cuticle [Gams, W. & Jansson, H. B. (1985). *Mycotaxon* 22, 33–38; Dijksterhuis, J., Veenhuis, M. & Harder, W. (1990). *Mycological Research* 94, 1–8.]

*E. vermicola* is the first recorded endoparasite of the pinewood nematode. It exhibits high infectivity towards the pinewood nematode. In vitro, a population of pinewood nematodes can be completely killed by *E. vermicola* in 8–10 days. Thus, *E. vermicola* is a biocontrol agent against the pinewood nematode.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Furthermore, from the above description, one skilled in the art can easily ascertain the essential characteristics of the present invention, and without departing from the spirit and scope thereof, can make various changes and modifications of the invention to adapt it to various usages and conditions.

What is claimed is:

1. A biologically pure fungal culture of Esetya sp. which has high infectivity toward a stem, leaf, bud, or flower nematode and has the identifying characteristics of producing a first type of conidiophores, conidiogenous cells, and conidia and a second type of conidiophores, conidiogenous cells, and conidia when grown in vivo or on a solid medium; wherein the first type of conidiophores is macronematous, mononematous, simple, erect, and broadly ampulliform; the first type of conidiogenous cells is integrated, phialidic, and rarely percurrent; and the first type of the conidia is solitary, one-celled, asymmetrically ellipsoidal, lunate, and concave; and the second type of conidiophore is macronematous, mononematous, simple or branched, cylindrical, subulate, and elongate; the second type of conidiogenous cells is integrated, phialidic, enteroblastic, terminal or intercalary, laterally proliferic, and indeterminate; and the second type of conidia is solitary, one-celled, bacilloid, and cylindrical.

2. The culture of claim 1 wherein blastospores are produced when grown in liquid broth.

3. The culture of claim 1, wherein the nematode is of the Bursaphelenchus, Aphelenchoides, Ditylenchus, or Phadinaphelenchus genus.

4. The culture of claim 3, wherein the nematode is of the Bursaphelenchus genus.

5. The culture of claim 3, wherein the nematode is of the *Bursaphelenchus xylophilus* species.

6. A biologically pure culture of *Esteya vermicola* which has high infectivity toward a stem, leaf, bud, or flower nematode and has the identifying characteristics of producing a first type of conidiophores, conidiogenous cells, and conidia and a second type of conidiophores, conidiogenous cells, and conidia when grown in vivo and on a solid medium; wherein the first type of conidiophores is macronematous, mononematous, simple, erect, broadly ampulliform, tapering upward into a thin neck, subhyaline to greyish green, and smooth, roughened to very roughened; the first type of conidiogenous cells is integrated, phialidic, and rarely percurrent; and the first type of conidia is solitary, one-celled, asymmetrically ellipsoidal, lunate, concave, hyaline, smooth-walled, and adhesive, and ends moderately apiculate and contains an endospore-like structure; and the second type of conidiophores is macronematous, mononematous, simple or branched, erect, cylindrical, subulate, septate, hyaline, subhyaline to greyish green, smooth, roughened to very roughened, and is somewhat swollen at the base; the second type of conidiogenous cells is integrated, phialidic, enteroblastic, terminal or intercalary, laterally proliferic, and indeterminate; and the second type of conidia is solitary, slimy, one-celled, bacilloid, cylindrical, hyaline, smooth, and non-adhesive, and often aggregates at the apex forming false head.

7. The culture of claim 6, wherein blastospores are produced when grown in liquid broth.

8. The culture of claim 6, wherein the nematode is of the Bursaphelenchus, Aphelenchoides, Ditylenchus, or Phadinaphelenchus genus.

9. The culture of claim 6, wherein the nematode is of the Bursaphelenchus genus.

10. The culture of claim 9, wherein the nematode is of the *Bursaphelenchus xylophilus* species.

11. The culture of claim 1, wherein the culture, when grown in vivo, the first type of conidiophores, conidiogenous cells, and conidia predominates and the nematode is parasitized by the first type of conidia.

12. The culture of claim 6, wherein the culture when grown in vivo, the first type of conidiophores, conidiogenous cells, and conidia predominates and the nematode is parasitized by the first type of conidia.

13. A biologically pure culture of *Esteya vermicola* deposited with the American Type Culture Collection on Jan. 29, 1999 and assigned accession number 74485; or a mutant derived therefrom.

14. A biologically pure culture of *Esteya vermicola* having all of the identifying characteristics of the strain deposited with the American Type Culture Collection on Jan. 29, 1999 and assigned accession number 74485.

15. A biologically pure fungal culture of Esteya sp. which has the identifying characteristics of producing a first type of conidiophores, conidiogenous cells, and conidia and a second type of conidiophores, conidiogenous cells, and conidia when grown in vivo or on a solid medium; wherein the first type of conidiophores is macronematous, mononematous, simple, erect, and broadly ampulliform; the first type of conidiogenous cells is integrated, phialidic, and rarely percurrent; and the first type of the conidia is solitary, one-celled, asymmetrically ellipsoidal, lunate, and concave; and the second type of conidiophore is macronematous, mononematous, simple or branched, cylindrical, subulate, and elongate; the second type of conidiogenous cells is integrated, phialidic, enteroblastic, terminal or intercalary, laterally proliferic, and indeterminate; and the second type of conidia is solitary, one-celled, bacilloid, and cylindrical.

16. A biologically pure culture of Esteya sp. which has the identifying characteristics of producing a first type of conidiophores, conidiogenous cells, and conidia and a second type of conidiophores, conidiogenous cells, and conidia when grown in vivo and on a solid medium; wherein the first type of conidiophores is macronematous, mononematous, simple, erect, broadly ampulliform, tapering upward into a thin neck, subhyaline to greyish green, and smooth, roughened to very roughened; the first type of conidiogenous cells is integrated, phialidic, and rarely percurrent; and the first type of conidia is solitary, one-celled, asymmetrically ellipsoidal, lunate, concave, hyaline, smooth-walled, and adhesive, and ends moderately apiculate and contains an endospore-like structure; and the second type of conidiophores is macronematous, mononematous, simple or branched, erect, cylindrical, subulate, septate, hyaline, subhyaline to greyish green, smooth, roughened to very roughened, and is somewhat swollen at the base; the second type of conidiogenous cells is integrated, phialidic, enteroblastic, terminal or intercalary, laterally proliferic, and indeterminate; and the second type of conidia is solitary, slimy, one-celled, bacilloid, cylindrical, hyaline, smooth, and non-adhesive, and often aggregates at the apex forming false head.

* * * * *